US00PP26140P2

(12) United States Plant Patent
Verwer

(10) Patent No.: US PP26,140 P2
(45) Date of Patent: Nov. 24, 2015

(54) ***DAHLIA* PLANT NAMED 'HDCHR23'**

(50) Latin Name: *Dahlia hybrida*
Varietal Denomination: HDCHR23

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 38 days.

(21) Appl. No.: 13/986,656

(22) Filed: May 21, 2013

(51) Int. Cl.
*A01H 5/02* (2006.01)

(52) U.S. Cl.
USPC ..... Plt./321

(58) Field of Classification Search
USPC ..... Plt./321
CPC ..... A01H 5/025; A01H 5/00
See application file for complete search history.

(56) References Cited

PUBLICATIONS

Upov Pluto Plant Variety Database 20141107, retrieved on Nov. 12, 2014, retrieved from the Internet at <www3.wipo.int/pluto/user/en/index.jsp> one page.*

* cited by examiner

*Primary Examiner* — June Hwu
(74) *Attorney, Agent, or Firm* — C. A. Whealy

(57) ABSTRACT

A new and distinct cultivar of *Dahlia* plant named 'HDCHR23', characterized by its compact, mounding and dense plant habit; serrated dark-colored leaves; freely flowering habit; daisy-type inflorescence form; large inflorescences with red purple-colored ray florets; and good postproduction longevity.

2 Drawing Sheets

Botanical designation: *Dahlia hybrida.*
Cultivar denomination: 'HDCHR23'.

BACKGROUND OF THE INVENTION

The present invention relates to a new and distinct cultivar of *Dahlia* plant, botanically known as *Dahlia hybrida*, and hereinafter referred to by the name 'HDCHR23'.

The new *Dahlia* plant is a product of a planned breeding program conducted by the Inventor in Lisse, The Netherlands. The objective of the breeding program is to create new compact container *Dahlia* plants with dark-colored leaves, large inflorescences and good postproduction longevity.

The new *Dahlia* plant originated from an open-pollination in Lisse, The Netherlands in 2008 of a proprietary seedling selection of *Dahlia hybrida* identified as code number VR7-205, not patented, as the female, or seed, parent with a proprietary selection of *Dahlia hybrida* identified as code number VD5-272, not patented, as the male, or pollen, parent. The new *Dahlia* plant was discovered and selected by the Inventor as a single flowering plant from within the progeny of the stated open-pollination in a controlled greenhouse environment in Lisse, The Netherlands in 2009.

Asexual reproduction of the new *Dahlia* plant by terminal vegetative cuttings since the spring of 2010 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'HDCHR23'. These characteristics in combination distinguish 'HDCHR23' as a new and distinct *Dahlia* plant:

1. Compact, mounding and dense plant habit.
2. Serrated dark-colored leaves.
3. Freely flowering habit.
4. Daisy-type inflorescence form.
5. Large inflorescences with red purple-colored ray florets.
6. Good postproduction longevity.

Plants of the new *Dahlia* differ primarily from plants of the female parent selection in the following characteristics:

1. Plants of the new *Dahlia* are more compact and denser than plants of the female parent selection.
2. Leaves of plants of the new *Dahlia* are darker in color than leaves of plants of the female parent selection.
3. Plants of the new *Dahlia* and the female parent selection differ in ray floret color as plants of the female parent selection have reddish brown-colored ray florets.

Plants of the new *Dahlia* differ primarily from plants of the male parent selection in the following characteristics:

1. Plants of the new *Dahlia* are more compact and denser than plants of the male parent selection.
2. Plants of the new *Dahlia* are more freely branching than plants of the male parent selection.
3. Leaves of plants of the new *Dahlia* are darker in color than leaves of plants of the male parent selection.
4. Plants of the new *Dahlia* have smaller inflorescences than plants of the male parent selection.
5. Plants of the new *Dahlia* and the male parent selection differ in ray floret color as plants of the male parent selection have red-colored ray florets.

Plants of the new *Dahlia* can be compared to plants of the *Dahlia hybrida* 'HDPU165', disclosed in U.S. Plant Pat. No. 23,299. In side-by-side comparisons conducted in Lisse, The Netherlands, plants of the new *Dahlia* differed from plants of 'HDPU165' in the following characteristics:

1. Plants of the new *Dahlia* were more compact than plants of 'HDPU165'.
2. Plants of the new *Dahlia* had larger leaves than plants of 'HDPU165'.
3. Plants of the new *Dahlia* and 'HDPU165' differed in ray and disc floret color.
4. Plants of the new *Dahlia* had longer peduncles than plants of 'HDPU165'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of typical flowering plants of 'HDCHR23' grown in an outdoor nursery.

The photograph on the second sheet is a close-up view of a typical flowering plant of 'HDCHR23'.

DETAILED BOTANICAL DESCRIPTION

The photographs and following observations and measurements describe plants grown during the late summer and early autumn in 15-cm containers in an outdoor nursery in Lisse, The Netherlands and under cultural practices typical of commercial container *Dahlia* production. During the production of the plants, day temperatures ranged from 15° C. to 30° C. and night temperatures ranged from 10° C. to 20° C. Plants were pinched one time about three weeks after planting. Plants were four months old when the photographs and description were taken. In the following description, color references are made to The Royal Horticultural Society Colour Chart, 1995 Edition, except where general terms of ordinary dictionary significance are used.

Botanical classification: *Dahlia hybrida* 'HDCHR23'.

Parentage:

*Female, or seed, parent*.—Proprietary seedling selection of *Dahlia hybrida* identified as code number VR7-205, not patented.

*Male, or pollen, parent*.—Proprietary selection of *Dahlia hybrida* identified as code number VD5-272, not patented.

Propagation:

*Type*.—By terminal vegetative cuttings.

*Time to initiate roots, summer*.—About eleven days at soil temperatures of 15° C.

*Time to initiate roots, winter*.—About 13 days at soil temperatures of 15° C.

*Time to produce a rooted young plant, summer*.—About 20 days at soil temperatures of 15° C.

*Time to produce a rooted young plant, winter*.—About 24 days at soil temperatures of 15° C.

*Root description*.—Fine, fleshy; white in color.

*Rooting habit*.—Moderately freely branching; dense.

*Tubers*.—Length: About 18 cm. Diameter: About 13 cm. Texture: Corky. Color: Close to 199B.

Plant description:

*Plant and growth habit*.—Compact and mounding plant habit; inverted triangular plant form; freely basal branching with about seven lateral branches per plant; dense and bushy appearance; inflorescences held above the foliar plane on strong peduncles; vigorous growth habit.

*Plant height*.—About 32 cm.

*Plant diameter or spread*.—About 30 cm.

*Lateral branches*.—Length: About 28 cm to 30 cm. Diameter: About 1.6 cm. Internode length: About 3 cm to 16 cm. Texture: Smooth, glabrous. Strength: Strong. Color: Close to 187A.

Leaf description:

*Arrangement*.—Opposite, single or compound with three or five leaflets, not winged.

*Leaf length*.—About 9 cm to 17 cm.

*Leaf width*.—About 3.5 cm to 12 cm.

*Shape*.—Ovate.

*Apex*.—Acute.

*Base*.—Attenuate.

*Margin*.—Serrate to somewhat sinuate; sinuses divergent.

*Venation pattern*.—Pinnate.

*Texture, upper and lower surfaces*.—Smooth, glabrous.

*Color*.—Developing leaves, upper surface: Close to 147A. Developing leaves, lower surface: Close to or darker than 191A. Fully expanded leaves, upper surface: Close to 147A tinted with close to 200A; venation, close to 187B. Fully expanded leaves, lower surface: Close to 148B; venation, close to 147B.

*Petioles*.—Length, all leaves and leaflets: About 3.5 cm to 6 cm. Diameter, all leaves and leaflets: About 2 mm to 6 mm. Texture, upper and lower surfaces: Smooth, glabrous. Color, upper surface: Close to 187B. Color, lower surface: Close to 148A.

Inflorescence description:

*Appearance and flowering habit*.—Rotate daisy-type inflorescences with ray and disc florets developing acropetally on a receptacle; inflorescences positioned above and beyond the foliar plane on strong peduncles; inflorescences face mostly upright; freely flowering habit with typically about twelve open inflorescences and 23 inflorescence buds per plant.

*Fragrance*.—None detected.

*Time to flower*.—Plants begin flowering about 70 days after planting; flowering continuous during the summer and autumn in The Netherlands.

*Post-production longevity*.—Good postproduction longevity; inflorescences maintain good substance for about 15 days on the plant and for about five days as a cut flower; inflorescences persistent.

*Inflorescence buds*.—Height: About 1.5 cm. Diameter: About 1.7 cm. Shape: Oblate. Color: Towards the base, close to 200A; mid-section, close to 187A; towards the apex, close to 71A.

*Inflorescence diameter*.—About 8.5 cm.

*Inflorescence depth* (*height*).—About 2 cm.

*Disc diameter*.—About 2.3 cm.

*Receptacle height*.—About 6 mm.

*Receptacle diameter*.—About 1.8 cm.

*Receptacle color*.—Close to 187A.

*Ray florets*.—Length: About 3.7 cm. Width: About 2.1 cm. Shape: Ovate. Apex: Mucronulate. Base: Attenuate. Margin: Entire. Aspect: Initially upright to roughly perpendicular to the peduncle; mostly flat and straight, not twisting. Texture, upper and lower surfaces: Smooth, glabrous; velvety. Number of ray florets per inflorescence: About eight arranged in a single whorl. Color: When opening, upper surface: Close to 59A; towards the apex, close to 59B. When opening, lower surface: Close to 59B; center, close to 77A. Fully opened, upper surface: Close to 60A blushed with close to 53A; color does not fade with development. Fully opened, lower surface: Close to 60B; center, close to 74A; color does not fade with development.

*Disc florets*.—Shape: Tubular; apex dentate. Length: About 1.3 cm. Diameter: About 1.5 mm. Number of disc florets per inflorescence: About 90. Color, immature: Apex: Close to 187B. Mid-section: Close to 185B. Base: Close to 150B. Color, mature: Apex: Close to 22A. Mid-section: Close to 185B. Base: Close to 150B.

*Phyllaries*.—Quantity per inflorescence: About five arranged in a single whorl. Length: About 1.2 cm. Width: About 4 mm. Shape: Ovate to lanceolate. Apex: Acute. Base: Attenuate. Margin: Entire. Texture, upper and lower surfaces: Smooth, glabrous. Color, upper and lower surfaces: Close to 200A.

*Peduncles*.—Length, terminal peduncle: About 1.2 cm. Length, fourth peduncle: About 1.6 cm. Diameter: About 3 mm. Strength: Strong. Aspect: About 70° to 80° from vertical. Texture: Smooth, glabrous. Color: Close to 187B.

*Reproductive organs*.—Androecium, present on disc florets only: Quantity per disc floret: Five. Filament length: About 4 mm. Filament color: Close to 2B. Anther shape: Lanceolate. Anther length: About 1.5 mm. Anther color: Close to 17B. Pollen amount: Abundant. Pollen color: Close to 21A. Gynoecium, present on ray and disc florets: Quantity per floret: One. Pistil length: About 5 mm. Stigma shape: Lanceolate. Stigma color: Close to 11B. Style length: About 8 mm. Style color: Close to 1C. Ovary color: Close to 1D. Fruits: Length: About 1.6 cm. Diameter: About 1.5 cm. Texture: Smooth, glabrous. Color: Close to 187B. Seeds: Length: About 5 mm. Diameter: About 7 mm. Color: Close to 187B.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 40° C.

It is claimed:

1. A new and distinct *Dahlia* plant named 'HDCHR23' as illustrated and described.

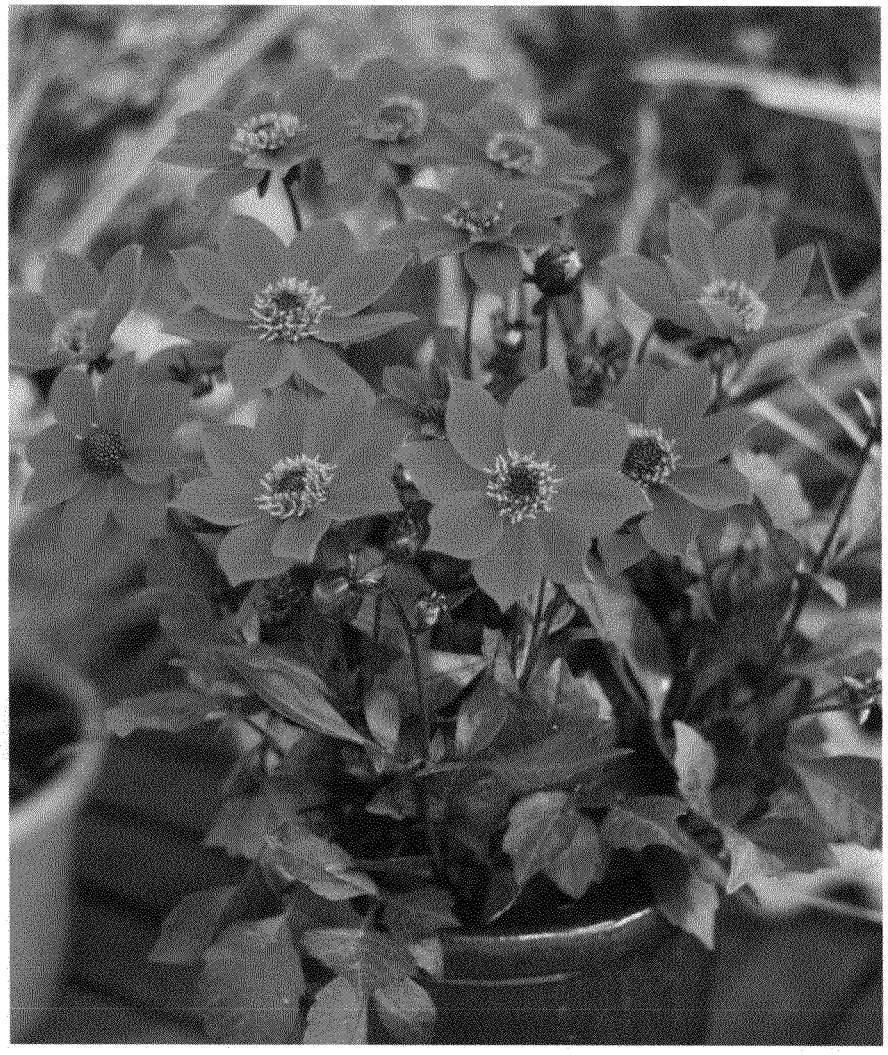

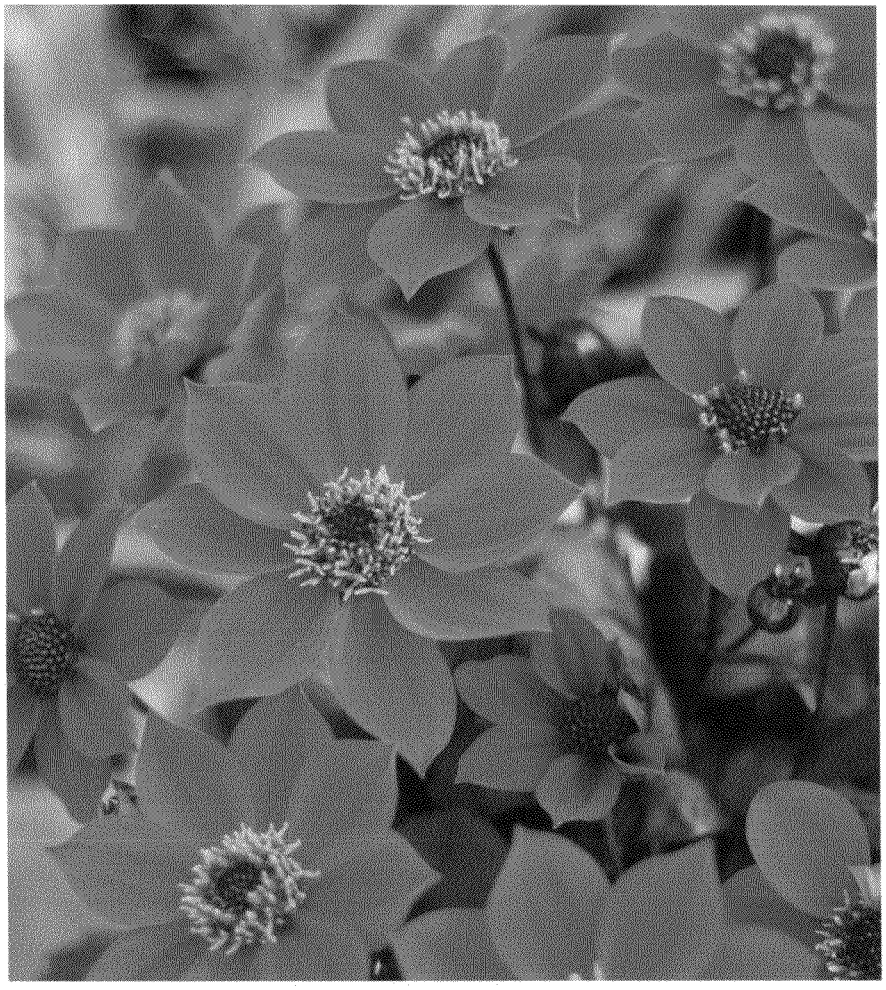

* * * * *